United States Patent
Ferrero et al.

(10) Patent No.: US 6,820,014 B2
(45) Date of Patent: Nov. 16, 2004

(54) METHOD FOR DETERMINATION OF REALISTIC UV PROTECTION FACTORS OR BROAD SPECTRUM INDICES

(75) Inventors: Louis Ferrero, Nice (FR); Marc Pissavini, Nice (FR); Leonhard Zastrow, Monaco (MC)

(73) Assignee: Coty B.V. (NL)

( * ) Notice: Subject to any disclaimer, the term of this patent is extended or adjusted under 35 U.S.C. 154(b) by 87 days.

(21) Appl. No.: 10/323,088

(22) Filed: Dec. 18, 2002

(65) Prior Publication Data

US 2003/0157039 A1 Aug. 21, 2003

(30) Foreign Application Priority Data

Dec. 20, 2001 (DE) .......................................... 101 64 469

(51) Int. Cl.[7] .............................................. Q01N 31/00
(52) U.S. Cl. .......................... 702/28; 250/372; 250/373
(58) Field of Search .............................. 250/372, 474.1, 250/373; 600/407; 702/28

(56) References Cited

U.S. PATENT DOCUMENTS 5,640,957 A * 6/1997 Kaminski et al. ........... 600/407
5,691,158 A * 11/1997 Reece et al. ................ 435/7.92

* cited by examiner

*Primary Examiner*—John Barlow
*Assistant Examiner*—Stephen J. Cherry
(74) *Attorney, Agent, or Firm*—Pendorf & Cutliff

(57) ABSTRACT

The invention relates to a new method for determination of realistic UV protection factors or bread spectrum indices of a sunscreen preparation. Realistic UV protection factors are calculable by determination of the theoretical and the experimental UV absorbances of known UV filters in wavelength steps of about 5 nm in the range of 290–400 nm from a definite basic formulation (emulsion, gel etc.) and on a transparent substrate and introducing of the values in a mathematical model. These factors are in conformity with values measured in vivo. The number of the experiments for developing new formulations are significant reduced because only basic formulation, kind and concentration of the filters have to enter.

11 Claims, 4 Drawing Sheets

Figure 1:
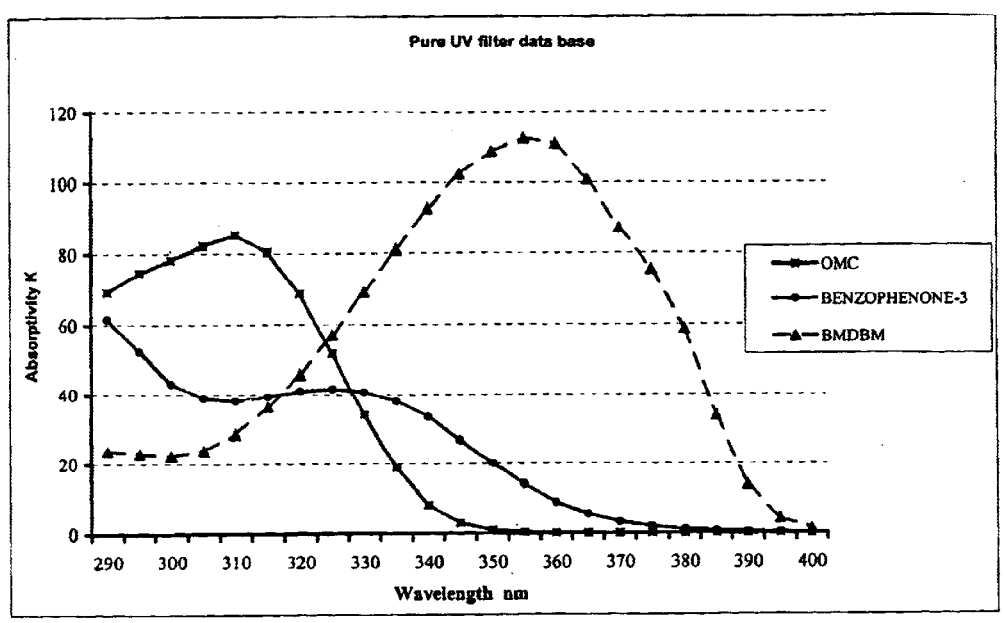

METHOD FOR DETERMINATION OF REALISTIC UV PROTECTION FACTORS OR BROAD SPECTRUM INDICES

The present invention relates to a new method for determination of realistic UV protection factors or broad spectrum indices of a sunscreen preparation.

Numerous attempts have been made to understand how sunscreen preparations protect against UV radiations e.g. Int.J.Cosmet.Sci., 7, 235–246 (1985). Normally, the final UV protection achieved by a sunscreen product should be the result of each filter UV absorption present in the preparation. To determine it, the simplest way is to add each UV filter Absorbance, measured in diluted solution, wavelength by wavelength, according to Beer-Lambert law's. However, it is now trivial to remark the poor correlation between the SPF(s) directly calculated from this method and the real SPF(s): several magnitude orders of difference, much too high for the calculation.

Recently, with the generalization of the in vitro SPF method, realistic experimental UV data has been easily obtained on the whole erythemal wavelength range (from 290 to 400 nm). This recent instrumental UV spectroscopy is based on the assessment of diffuse transmission through a film of sunscreen preparation, directly spread on an uneven transparent substrates, chosen to resemble skin topography, for example the surgical Transpore® tape manufactured by the 3M Company. As a result, a good correlation between the SPF, derived from these experimental in vitro curves, and the in vivo SPF has been successfully obtained. However, although the method was revealed to be a very useful tool for the formulator, there is little logic in the relationship between the amount of active ingredients (UV absorbers) introduced in the sunscreen product and the final UV absorption. The main reason comes from the non-relevance of the Beer-Lambert law for the UV transmission spectroscopy of irregular thin films.

So, until now, it seemed impossible to predict any protection factor from a new blend of UV filters. The only solution was to achieve a complete sunscreen formulation and to test it by the in vitro method. Therefore, formulators were always obliged to numerous fastidious assays to optimize their UV filter combination, according to the SPF or the UVA protection targeted.

Object of the present invention is a new method for determination of realistic UV protection factors or broad spectrum indices of a sunscreen preparation according to the amount of active UV absorbents introduced in a sunscreen formulation.

Surprisingly, it was discovered now that one is able to establish a mathematical relationship between the theoretical Absorbance curve of a sunscreen preparation, calculated by applying the Beer-Lambert law to UV filter composition, and the experimental Absorbance curve obtained through in vitro spectroscopy assays. Very interestingly, this relationship was found to depend on very few parameters, all related to experimental in vitro spectroscopy:

the nature and the roughness of the transparent substrate on which a thin film of sunscreen preparation was spread for assessment of diffuse transmission the amount of sunscreen deposited the type of vehicle in which UV filters are incorporated.

Substrates with a roughened upper surface are chosen to simulate the porosity and texture of human skin. As already mentioned in literature, surface irregularities play a major role in influencing the photo-protection of a topical sunscreen product. The amount of deposited sunscreen is carefully determined in order to obtain a good correlation with in vivo SPF. Like in the real SPF, the base in which UV filters are incorporated can also modify the final protection.

One time the previous relationship defined, the sole variable to be considered is the theoretical Absorbance, whatever the wavelength associated with it. So, unrealistic calculated UV data, according to Beer-Lambert's law, can be easily converted into realistic UV data, from which all kinds of protection factors and broad spectrum indices can be calculated. The following schema can help to understand the different calculation steps:

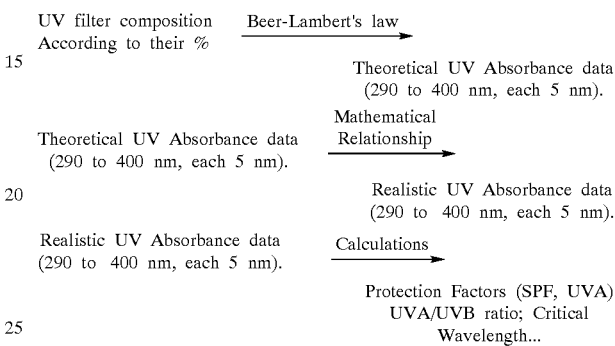

Realistic UV Absorbance data means that these calculated data are identical to the ones which could be obtained by achieving in vitro assays.

The mathematical relationship should be previously determined, by plotting experimental in vitro Absorbance data versus theoretical Absorbance data, from selected sunscreen preparations. Specific relationship can be obtained, according to the type of vehicle involved: O/W emulsion, W/O emulsion, Gel emulsion etc. in order to take into account the vehicle effect.

The drawings show:

FIG. 1 a graph of UV Absorptivity of different UV filters at different wavelengths.

Figure 2:
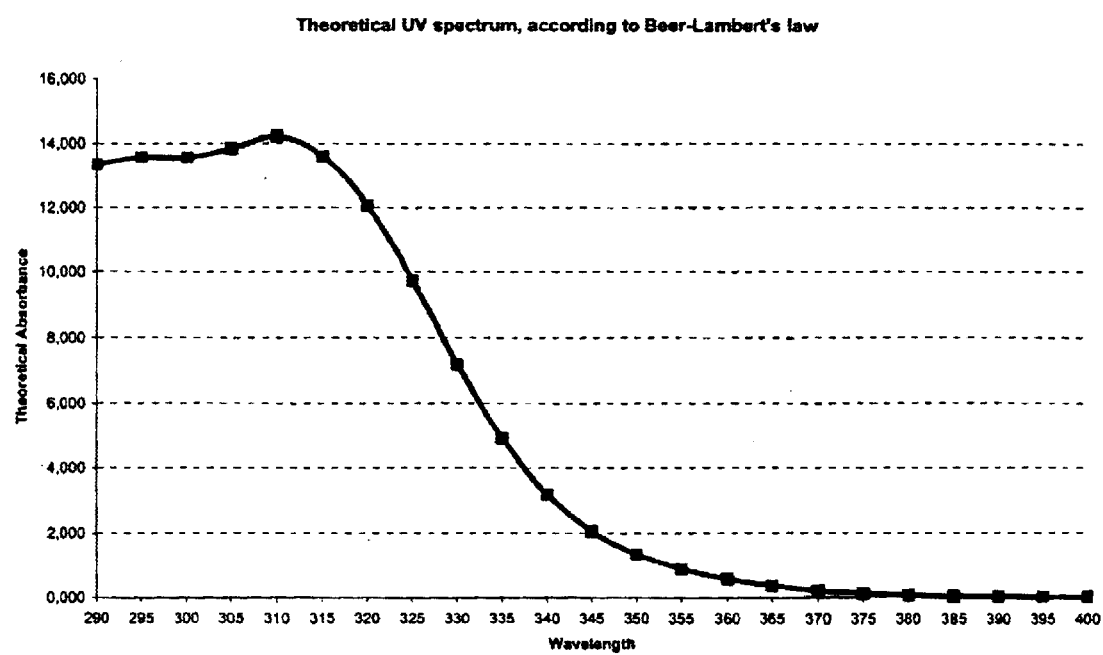

FIG. 2 a graph showing a theoretical UV spectrum, calculated according to Beer-Lambert's Law.

Figure 3:
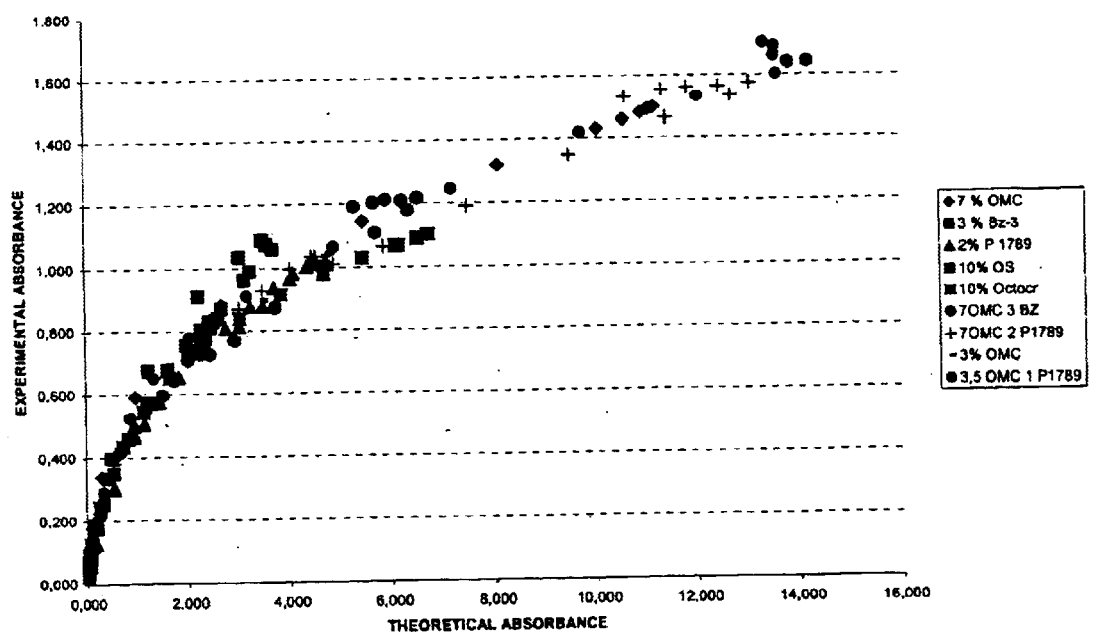

FIG. 3 a graph showing the relationship between experimental Absorbance data and theoretical Absorbance data from different products F1 to F8.

Figure 4:
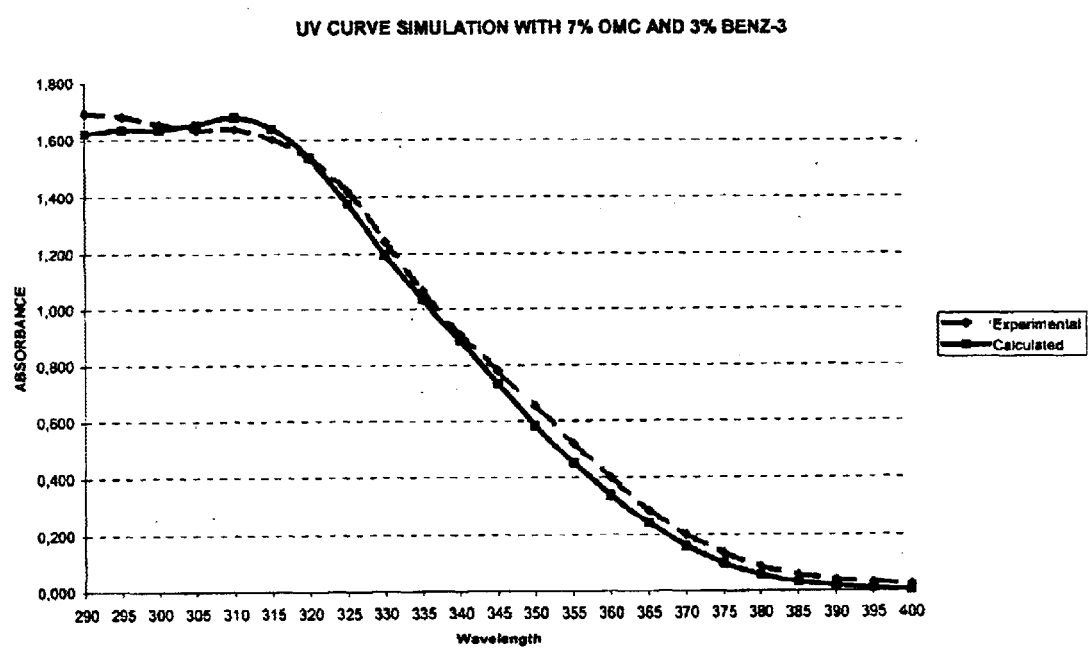

FIG. 4 an example of UV curve simulation with 7% Octyl methoxycinnamate and 3% Benzophenone-3, according to the mathematical relationship.

The method for prediction of realistic UV protection factors of a sunscreen preparation of the invention comprises:

(1) Determination of Absorptivities of pure known organic or inorganic UV filter substances in a pure organic solvent or a mixture thereof, at wavelengths from 290 to 400 nm, in wavelength steps in the range of 1–10 nm, preferably of 5 nm;

(2) Calculation of the theoretical UV Absorbances $A_{(\lambda)th}$, from 290 to 400 nm, in wavelength steps in the range of 1–10 nm, preferably of 5 nm, of some pure UV filter substances or mixtures thereof which are contained in different amounts in a defined basic formulation, according to application of Beer-Lambert law to the Absorptivities previously determined in step (1) by using the following equation:

$$A_{(\lambda)th} = w * 1/100 * \sum_{n=1}^{n=p} K_{\lambda(n)} * a_{(n)} \quad [1]$$

wherein n is the number of UV filter substances from n=1 to n=p, w is the initial surface density of the sunscreen preparation immediately after deposition on an uneven transparent substrate in mg/cm$^2$, $K_{\lambda(n)}$ is the Absorptivity of the number n of UV filter substances at a wavelength λ and a(n) is the amount of the UV filter substance in the sunscreen preparation in % by weight;

(3) Determination of the experimental UV Absorbances $A_{(\lambda)exp}$, from 290 to 400 nm, in wavelength steps of 5 nm, of the UV filter substance or mixtures of substances of step (2), which has the same amount and is in the same basic formulation such as in step (2), which basic formulation is selected from the group consisting of the type O/W, W/O, oil, gel, stick, mousse, aerosol and ointment and wherein the formulation is deposited on an uneven transparent substrate, to achieve an irregular film of surface density of w mg/cm$^2$;

(3) Applying of pairs of experimental Absorbance data $A_{(\lambda)exp}$ of step (3) and theoretical Absorbance data $A_{(\lambda)th}$ of step (2) of the same wavelength in a graph;

(4) Determination of a mathematical function in correlation with the graph of step (4) by incorporation of parameters of an uneven film, which film represents a mathematical model of the application of a sunscreen preparation on a transparent substrate such as in step (3) and wherein by optimizing the fit to the pairs of Absorbance data, $A_{(\lambda)exp}$ versus $A_{(\lambda)th}$, through least squares error assessment, different area fractions $f_{(l)}$ to $f_{(i)}$ with different surface densities $w_{(l)}$ to w(i) are calculated, whereby applies:

$$\sum_{n=1}^{n=i} f(n) = 1 \text{ and}$$

$$\sum_{n=1}^{n=i} f(n) \cdot w(n) = w$$

wherein w is the initial surface density of the sunscreen preparation immediately after deposition on the transparent substrate, and wherein the mathematical function is:

$$A_{(\lambda)exp} = -\log\left[\sum_{n=1}^{n=i} f(n) \cdot 10^{-w(n) \cdot A(\lambda)th/w}\right] \quad [2]$$

Wherein $A_{(\lambda)th}$ is the calculated theoretical Absorbance according to step (2) and $A_{(\lambda)exp}$ is the experimental Absorbance according to step (3);

(5) Application of the method described in steps 1 to 5 to the prediction of realistic sun protection factors of a sunscreen preparation, previously to achieve any experimental in vitro or in vivo determination, wherein the following steps are involved:

(6) Calculation of the theoretical UV Absorbances $A_{(\lambda)th}$, from 290 to 400 nm, in wavelength steps of 5 nm, of an UV filter substance or mixture of substances which are contained in % amounts $a_l$ to $a_n$ in the sunscreen preparation of step (6), according to equation [1] of step (2);

(7) Calculation of realistic UV Absorbances $A_{(\lambda)real}$, from 290 to 400 nm, in wavelength steps in the range of 1–10 nm, preferably of 5 nm, according to the theoretical UV Absorbances calculated in step (7) and the mathematical function [2] of step (5), in which the area fractions $f_{(l)}$ to $f_{(i)}$ and the surface densities $w_{(l)}$ to $w_{(i)}$ were previously determined in step (5) for a basic formulation of the same type as the sunscreen preparation under study.

$$A_{(\lambda)real} = -\log\left[\sum_{n=1}^{n=i} f(n) \cdot 10^{-w(n) \cdot A(\lambda)th/w}\right] \quad [2a]$$

(8) Calculation of realistic sun protection factors of the sunscreen preparation of step (6) according to the equations:

$$SPF = \frac{\sum_{290}^{400} E_\lambda \cdot I_\lambda \cdot \Delta\lambda}{\sum_{290}^{400} E_\lambda \cdot I_\lambda \cdot T_\lambda \cdot \Delta\lambda} \quad [3]$$

wherein Tλ is the sunscreen transmittance at wavelength λ, whereby applies $T_\lambda = 10^{-A(\lambda)real}$, $E_\lambda$ is the spectral irradiance of terrestrial sunlight at wavelength λ expected for a clear sky at noon in midsummer for a latitude of 40° N, $I_\lambda$ is the erythema action spectrum.

The different steps of calculation should be detailed.

Step 1 and 2: Theoretical UV Absorbance Data Calculation Through Beer-Lambert's Law.

If a formulation contains p UV filters, numbered from n=1 to n=p, the resulting theoretical Absorbance at wavelength λ, for a surface density of w mg/cm$^2$, is:

$$A_{(\lambda)th} = w * 1/100 * \sum_{n=1}^{n=p} K_{\lambda(n)} * a_{(n)} \quad [1]$$

where $K_{\lambda(n)}$ is the Absorptivity of the number n UV filter at wavelength λ, and $a_{(n)}$ is its percentage in the sunscreen preparation. w corresponds to the amount of sunscreen deposited in mg/cm$^2$ onto the in vitro substrate. The calculation is repeated from 290 to 400 nm, each 5 nm (23 values).

Absorptivities of pure UV filters (=Absorbance normalized at 1 g/litre and 1 cm optical pathlength, so equivalent to 1 mg/cm$^2$) were previously measured, according to the following conditions:

Operating Conditions for Spectroscopy of Pure UV Filters in Diluted Solution:

A UV-VIS spectrophotometer was used to collect these UV data. An appropriate amount of pure UV filter was carefully diluted in a suitable solvent (e.g. in an organic solvent) and the transmittance spectrum of the solution was measured in a UV quartz cuvette. The Absorbance data (400–290 nm, 5 nm increment step) was normalized at 1 g/litre and 1 cm optical pathlength (Absorptivities $K_\lambda$) by using the Beer-Lambert law. Isopropanol was chosen for its polarity and its UV transparency in the following examples, but other solvents can be chosen, such as Hexane, Ethanol, n-Propanol, or cosmetic ester oils such as caprylic/capric triglyceride, or propylene glycol dicaprylate/dicaprate, both oils supplied under the names Miglyol 812 and Miglyol 840 by Condea Chemie.

A Data base is constituted which includes all types of suitable UV filters, for example UVB Filters: Octyl methoxycinnamate; Octocrylene; Octyl Salicylate; Phenylbenzylimidazole Sulphonic acid; 4-Methylbenzylidene Camphor; Dioctyl Butamido Triazone; Isoamyl p-Methoxycinnamate.

UVA and UVA/UVB Filters: Benzophenone-3; Butyl Methoxy Dibenzoylmethane; Methylene Bis-Benzoyltriazoyl Tetramethylbutylphenol.

Physical sunscreens: Zinc oxide and Titanium dioxide.

The UV Spectra of some UV filters present in the data base is presented in FIG. 1. Absorptivity data are plotted versus wavelength for each absorbent.

In FIG. 2, the theoretical UV spectrum of a film of sunscreen of 2 mg/cm$^2$, with e.g. 7% Octyl methoxycinnamate and 3% Benzophenone-3, was calculated, according to equation [1].

The intensity of UV absorption is obviously unrealistic: the calculated UV data achieve a SPF of 41 with an excessive Absorbance of 14 at 310 nm. A mathematical relationship should be found to convert the unrealistic calculated UV data into realistic UV data.

Step 3, 4 and 5: Mathematical Relationship Assessment

The relationship should be experimentally determined, according to the transparent substrate selected for in vitro spectroscopy, the amount of sunscreen deposited and the type of base in which UV filters are incorporated. The following example shows how it is possible to proceed.

Step 3: Determination of Experimental UV Absorbances.

As a UV transparent substrate it is preferred to use a non fluorescent, photo-stable, non reactive substrate which should distribute the product in a manner similar to human skin and so should have a textured upper surface. A preferred substrate is selected from the group consisting of the surgical tape Transpore®, Vitro Skin®, roughened quartz plate, roughened polymethylmethacrylate plate (PMMA) and excised human epidermis. In the following examples, sunscreens were spread on Transpore® tape to achieve a surface density of 2 mg/cm$^2$.

Different UV filters were tested, alone or combined, in the same O/W emulsion, according to the following table I:

TABLE I

UV Filters used in formulae F1 to F8. OMC = Octyl methoxycinnamate, OS = Octyl salicylate, OC = Octocrylene, BMDBM = Butyl methoxy dibenzoylmethane, Bz-3 = Benzophenone-3.

| UV filter combination | % OMC | % OS | % OC | % BMDBM | % Bz-3 |
|---|---|---|---|---|---|
| F1 | 3 | 0 | 0 | 0 | 0 |
| F2 | 7 | 0 | 0 | 0 | 0 |
| F3 | 0 | 10 | 0 | 0 | 0 |
| F4 | 0 | 0 | 10 | 0 | 0 |
| F5 | 0 | 0 | 0 | 2 | 0 |
| F6 | 0 | 0 | 0 | 0 | 3 |
| F7 | 7 | 0 | 0 | 0 | 3 |
| F8 | 7 | 0 | 0 | 2 | 0 |

Experimental In Vitro Spectroscopy: An appropriate volume of sunscreen preparation was deposited on the transparent substrate to achieve a surface density of 2 mg/cm$^2$; see for the deposition also *J. Soc. Cosmet. Chem.*, 40, 127–133 (1989). After application, the product was immediately spread over the whole surface, using light strokes with a glove. Transmittance data (from 290 to 400 nm, each 5 nm) of each treated substrate was carefully measured by a Labsphere UV-1000 S Transmittance analyzer; 3 to 5 different substrates were used for each experiment. A non treated substrate was taken as a reference.

The experimental Absorbance data was directly deduced from the experimental transmittance data. Simultaneously, Theoretical Absorbance data was calculated, according to equation [1].

Step 4 and 5: Relationship Assessment

Pairs of experimental and theoretical Absorbance data, taken at each wavelength, were determined for each product and plotted. Thus, UV data from products F1 to F8 could be combined into a same graph—see FIG. 3.

It is to note that all the data are grouped on a single curve, whichever the sunscreen or the wavelength considered. A simple relationship between Theoretical and Experimental Absorbance was thus demonstrated.

We can also remark the non linearity of the relationship. Experimental data is more attenuated in the high values than in the low ones. This explains the special shape of the UV curves obtained through in vitro spectroscopy.

Any mathematical function, which achieves a good correlation with the pairs of experimental and theoretical Absorbance data, can be proposed. Among a lot of available functions (cf. Polynomial of 5th power function or Power law function), it was found with the present invention a special function, particularly well suited to our purpose: the uneven film model, a mathematical approach which was previously proposed by O'Neill, *J. Pharm. Sci.*, 7, 888–891 (1983), to calculate the % of transmitted light through an irregular film of absorbing material. We already used the same uneven film model to explain the special shape of in vitro UV curves (Ferrero L., Orcet A. M., Zastrow L., Proceedings of the 20$^{th}$ IFSCC Congress, Cannes, France, Poster P028 (1998). A very simple film with only two levels was initially proposed by O'Neill. A general equation is now given, which does not limit the number of film area fractions f(n) with different sunscreen surface densities w(n), whereby applies:

$$\sum_{n=1}^{n=i} f(n) = 1 \text{ and}$$

$$\sum_{n=1}^{n=i} f(n) \cdot w(n) = w$$

wherein w is the initial surface density of the sunscreen preparation immediately after deposition on the transparent substrate, and wherein the mathematical function is:

$$A_{(\lambda)exp} = -\log\left[\sum_{n=1}^{n=i} f(n) \cdot 10^{-w(n) \cdot A(\lambda)th/w}\right] \quad [2]$$

Wherein $A_{(\lambda)th}$ is the calculated theoretical Absorbance according to step (2) and $A_{(\lambda)exp}$ is the experimental Absorbance according to step (3);

An irregular 3 level film model (n=3) can generally achieve a good fit with the sunscreen UV data. According to the best correlation with the graph, the 3 different area fractions and the 3 different surface densities are determined through least squares error assessment. As an example, results are given for F1 to F8 formulations spread on Transpore® tape:

$f_1 = 0.2649 \quad w_1 = 5.2216 \text{ mg/cm}^2 \quad \text{with } w = 2 \text{ mg/cm}^2$ $f_2 = 0.5348 \quad w_2 = 1.1019 \text{ mg/cm}^2$ $f_3 = 0.2004 \quad w_3 = 0.1388 \text{ mg/cm}^2$ A refinement of the method in step 4–5 is to use, instead of the discontinuous step film model, a continuous film model with an infinite number of surface densities and area fractions.

To realise that, a surface density function $W_{(F)}$ should be defined, the function variable being F, cumulative fraction of unit area, which is a number between 0 and 1.

We obviously have:

$$\int_0^1 dF = 1$$

dF replacing the fraction areas f(n) previously used in the discontinuous model.

$$\int_0^1 W_{(F)} \times dF = w$$

wherein w is the initial surface density of the sunscreen preparation deposited on the transparent substrate, $W_{(F)}$ being the surface density function. The mathematical relationship becomes:

$$A_{(\lambda)exp} = -\log\left[\int_0^1 10^{-W_{(F)} \times A\lambda th/w} \times dF\right]$$ [2b]

wherein $A_{\lambda,th}$ is the calculated theoretical Absorbance according to step (2) and $A_{(\lambda)exp}$ is the experimental Absorbance according to step (3).

Correlation between both Absorbance data can be achieved through numerical integration of equation [2b], from F=0 to F=1.

Surface density function $W_{(F)}$ should be chosen among functions to parametrize. Thus, the function parameters can be optimised through least square error assessment in order to calculate realistic Absorbance data very close to the experimental Absorbance data.

A simple polynomial function can be advantageous used:

$$W_{(F)} = a \times (p \times F^{0.5} + q \times F + r \times F^2)$$

With: $p+q+r=1$ and:

$$a = \frac{6 \times w}{4 \times p + 3 \times q + 2 \times r}$$

Step 6–9: Application to Prediction of Protection Factors and Broad Spectrum Indices.

The values for f1, f2 and f3 etc. depends on the kind of the basic formulation (e.g. emulsion or gel) and the properties of the substrate. For the latter is important the roughness of the surface (e.g. Transpore® Ra 11.3 µm, PMMA Ra 5.7 82 m, quartz Ra 0.6 µm, VitroSkin® hydrate ra 3.0 µm; Ra=arithmetic average of the surface roughness), whereby the roughness of the surface can be balanced by the amount of the applied sunscreen preparation. The amount of applied sunscreen preparation should be in the range of 0.5–3 mg/cm², preferably 1.2–2 mg/cm² because in this way a good agreement can be realized with the in vivo results. In the present invention are worked with 2 mg/cm².

One time the mathematical relationship validated, any new UV filter combination present in the same type of base used for the relationship assessment can be treated: Theoretical Absorbance data $A_{(\lambda)th}$, calculated through equation [1], is converted into Realistic Absorbance data $A_{(\lambda)real}$, through equation [2a], in which area fractions f(n) and surface densities w(n) were previously determined.

$$A_{(\lambda)real} = -\log\left[\sum_{n=1}^{n=i} f(n) \cdot 10^{-w(n) \cdot A(\lambda)th/w}\right]$$ [2a]

Protection Factors and Broad spectrum indices are then deduced from the calculated realistic Absorbance data.

For each considered wavelength, the realistic Absorbance data is first transformed into Transmittance data, via the simple mathematical relation:

$$T_\lambda = 10^{-A(\lambda)}$$

Any equation, previously reported by literature for in vitro spectroscopy [5], can be used. For example, the SPF calculation:

$$SPF = \frac{\sum_{290}^{400} E_\lambda \cdot I_\lambda \cdot \Delta\lambda}{\sum_{290}^{400} E_\lambda \cdot I_\lambda \cdot T_\lambda \cdot \Delta\lambda}$$ [3]

With: $T_\lambda$ is the sunscreen transmittance at wavelength $\lambda$.

$E_\lambda$=Spectral irradiance of terrestrial sunlight at wavelength $\lambda$, expected for a clear sky at noon in midsummer for a latitude of 40° N [6].

$I_\lambda$=Erythema action spectrum.

The wavelengths that are absorbed by a molecule or a combination of molecules to induce a specific photobiological reaction with greater or lesser efficiency constitute the action spectrum for that specific reaction.

The UVA Protection Factor:

$$PF\ UVA = \frac{\sum_{320}^{400} E_\lambda \cdot I_\lambda \cdot \Delta\lambda}{\sum_{320}^{400} E_\lambda \cdot I_\lambda \cdot T_\lambda \cdot \Delta\lambda}$$ [4]

With the same definitions as previously, excepted for $I_\lambda$, which can be the Immediate Pigment Darkening action spectrum or the Persistent Pigment Darkening action spectrum (biological UVA end points).

The equation used to calculate the ratio UVA/UVB:

$$UVA/UVB = \frac{\sum_{320}^{400} A_\lambda \cdot \Delta\lambda}{\sum_{290}^{320} A_\lambda \cdot \Delta\lambda}$$ [5]

Or the equation used to calculate the critical wavelength $\lambda c$.

$$0.90 = \frac{\sum_{290}^{\lambda c} A_\lambda \cdot \Delta\lambda}{\sum_{290}^{400} A_\lambda \cdot \Delta\lambda}$$ [6]

The list is not exhaustive. What is important is to calculate realistic Absorbance data, which cannot be achieved without the mathematical relationship we previously discovered.

The main advantage of the method is to reduce drastically the number of experimental assays required to achieve a sunscreen preparation. Formulators can immediately start their formulation with an optimized mixture of UV filters, according to the UV protection expected. Excessive concentrations are avoided because the method enables to choose, among the available UV filters, the best combination and to carefully adjust their concentrations.

EXAMPLES

To achieve a prediction, the percentage of each UV filter and the mathematical fit chosen to describe the relationship should be selected (parameters for equation [2a] in the example). SPF, ratio UVA/UVB and Protection Factors UVA and UVB are then deduced by applying steps 7, 8 and 9 of the method.

Example 1

It has been worked with an irregular film model for 3 levels (fraction areas). From the formulations F1–F8 are selected formulation 7 (7% OMC and 3% Benzophenone-3). The 3 different fraction areas and the 3 different surface densities were determined according to the best correlation method, through least squares error assessment. The following values according to table II and III were calculated.

| UV FILTERS | % |
|---|---|
| 1 Octyl Methoxycinnamate | 7 |
| 2 Octocrylene | 0 |
| 3 Octyl Salicylate | 0 |
| 4 P B S A | 0 |
| 5 Benzophenone-3 | 3 |
| 6 BMDBM | 0 |
| 7 Methylbenzilidene Camphor | 0 |
| 8 ZnO | 0 |
| 9 Dibenzotriazole | 0 |
| 10 TiO$_2$ | 0 |
| 11 Dioctyl butamido Triazone | 0 |
| 12 Isoamyl p-methoxycinnamate | 0 |
| Surface density mg/cm$^2$ | 2 |
| MATHEMATICAL RELATIONSHIP | |
| $f_1$ value | 0.2649 |
| $w_1$ value | 5.2216 |
| $f_2$ value | 0.5348 |
| $w_2$ value | 1.1019 |
| $f_3$ value | 0.2004 |
| $w_3$ value | 0.1388 |
| CALCULATED SPF | 17.65 |
| RATIO UVA /UVB | 0.3049 |
| PF UVA | 2.154 |
| PF UVB | 44.733 |

In FIG. 4, the calculated UV spectrum and the corresponding experimental UV spectrum of a mixture 7% OMC and 3% Benzophenone-3 are reported onto a same graph to show the quality of the Absorbance data simulation.

Example 2

Validation of the Method According to Formulations F1 to F8:

SPF and ratio UVA/UVB were simulated by the software, according to the different UV filter compositions reported in Table I. As shown in Table IV, predicted and experimental data are very close.

TABLE IV

Comparison between experimental and calculated data. Experimental SPF and UVA/UVB ratio were measured on products reported in table I, after spreading them on Transpore ® tape at 2 mg/cm$^2$.

| UV Filter Composition | | SPF Experimental | SPF Calculated | UVA/UVB RATIO Experimental | UVA/UVB RATIO Calculated |
|---|---|---|---|---|---|
| F1 OMC: | 3% | 6.15 | 6.46 | 0.161 | 0.195 |
| F2 OMC: | 7% | 10.54 | 10.99 | 0.183 | 0.202 |
| F3 OS: | 10% | 6.02 | 4.82 | 0.148 | 0.112 |
| F4 OCT: | 10% | 8.92 | 9.45 | 0.391 | 0.351 |
| F5 BMDBM: | 2% | 3.41 | 3.55 | 1.479 | 1.479 |
| F6 Bz-3: | 3% | 5.39 | 5.38 | 0.480 | 0.468 |
| F7 OMC: Bz-3: | 7% 3% | 18.39 | 17.64 | 0.328 | 0.305 |
| F8 OMC: BMDBM: | 7% 2% | 25.68 | 25.78 | 0.577 | 0.574 |

Example 3

Determination of SPF and ratio UVA/UVB, with further products. UV data and UV filter compositions are reported in Table V.

TABLE V

Comparison between experimental and calculated data. Experimental SPF and UVA/UVB ratio were measured after spreading the products on Transpore ® tape at 2 mg/cm$^2$.

| UV Filter Composition Example (2)–(8) | SPF Experimental | SPF Calculated | UVA/UVB RATIO Experimental | UVA/UVB RATIO Calculated |
|---|---|---|---|---|
| OMC: 5% BZ-3: 1% (2) BMDBM: 0.5% | 16.7 | 14.5 | 0.39 | 0.44 |
| OMC: 7.5% Bz-3: 2% (3) BMDBM: 0.5% | 25.2 | 23.2 | 0.37 | 0.40 |
| OMC: 7.5% Bz-3: 3% (4) OS: 3% BMDBM: 0.5% | 29.6 | 27.2 | 0.39 | 0.39 |
| OMC: 7.5% Bz-3: 3% (5) OS: 3% | 16 | 19.5 | 0.3 | 0.29 |
| OMC: 7.5% Bz-3: 3% (6) OS: 4% BMDBM: 1.4% | 39.8 | 36.6 | 0.49 | 0.48 |
| OMC: 7.5% Bz-3: 5% (7) OS: 5% BMDBM: 0.5% | 31.3 | 33.3 | 0.4 | 0.39 |
| OMC: 7.5% Bz-3: 2% (8) TiO2: 5% | 31 | 32.3 | 0.35 | 0.36 |

Example 4

Validation of the method according to formulations F1 to F8 in the same manner as in example 2 but with the method described in the second part of step 4–5 with variable F, function $W_F$ and the mathematical relationship [2a]:

As an example, p, q and r parameters were determined through least square error assessment, achieving a good fit with the sunscreen UV data of formulations F1 to F8:

p=0.07537
q=0
r=0.92463

SPF and ratio UVA/UVB were simulated by the software, according to the different UV filter compositions reported in Table I. As shown in Table IVa, predicted and experimental data are very close.

TABLE IVa

Comparison between both experimental and calculated data:
SPF and UVA/UVB ratio were measured on products reported in table I.

| UV Filter Composition | | SPF Experimental | SPF Calculated | UVA/UVB RATIO Experimental | UVA/UVB RATIO Calculated |
|---|---|---|---|---|---|
| F1 | OMC: 3% | 6.15 | 6.21 | 0.161 | 0.145 |
| F2 | OMC: 7% | 10.54 | 9.77 | 0.183 | 0.163 |
| F3 | OS: 10% | 6.02 | 5.01 | 0.148 | 0.112 |
| F4 | OCT: 10% | 8.92 | 10.28 | 0.391 | 0.352 |
| F5 | BMDBM: 2% | 3.41 | 3.89 | 1.479 | 1.423 |
| F6 | Bz-3: 3% | 5.39 | 5.61 | 0.480 | 0.478 |
| F7 | OMC: 7% Bz-3: 3% | 18.39 | 17.07 | 0.328 | 0.329 |
| F8 | OMC: 7% BMDBM: 2% | 25.68 | 25.13 | 0.577 | 0.605 |

What is claimed is:

1. A method for determining realistic UV protection factors or broad spectrum indices of a sunscreen preparation, which comprises:

(1) determining absorptivities of pure known UV filter substances in a pure solvent or a mixture of solvents, at wavelengths from 290 to 400 nm, in wavelength steps in the range of 1–10 nm;

(2) calculating theoretical UV absorbances $A_{(\lambda)th}$, from 290 to 400 nm, in wavelength steps in the range of 1–10 nm, of pure UV filter substances or mixtures thereof which are contained in different amounts in a defined basic formulation, according to application of Beer-Lambert law to the absorptivities previously determined in step (1) by using the following equation:

$$A_{(\lambda)th} = w * 1/100 * \sum_{n=1}^{n=p} K_{\lambda(n)} * a_{(n)} \qquad [1]$$

wherein n is the number of UV filter substances from n=1 to n=p, w is the initial surface density of the sunscreen preparation immediately after deposition on an uneven transparent substrate in mg/cm$^2$, $K_{\lambda(n)}$ is the absorptivity of the number n of UV filter substances at a wavelength $\lambda$ and a(n) is the amount of the UV filter substance in the sunscreen preparation in % by weight;

(3) determining experimental UV absorbances $A_{(\lambda)exp}$, from 290 to 400 nm, in wavelength steps in the range of 1–10 nm, of the UV filter substance or mixtures of substances of step (2), which has the same amount and is in the same basic formulation as in step (2), which formulation is selected from the group consisting of the type O/W, W/O, oil, gel, stick, mousse, aerosol and ointment and wherein the formulation is deposited on an uneven transparent substrate, to achieve an irregular film of a surface density of w mg/cm$^2$;

(4) applying pairs of experimental absorbance data $A_{(\lambda)exp}$ of step (3) and theoretical absorbance data $A_{(\lambda)th}$ of step (2) of the same wavelength in a graph;

(5) determining a mathematical function in correlation with the graph of step (4) by incorporation of parameters of an uneven film, which film represents a mathematical model of the application of a sunscreen preparation on a transparent substrate as in step (3) and wherein by optimizing the fit to the pairs of absorbance data, $A_{(\lambda)exp}$ versus $A_{(\lambda)th}$, through an error assessment, different area fractions $f_{(1)}$ to $f_{(i)}$ with different surface densities $W_{(1)}$ to $w_{(i)}$ are calculated, according to:

$$\sum_{n=1}^{n=i} f(n) = 1 \text{ and}$$

$$\sum_{n=1}^{n=i} f(n) \cdot w(n) = w$$

wherein w is the initial surface density of the sunscreen preparation immediately after deposition on the transparent substrate, and wherein the mathematical function is:

$$A_{(\lambda)exp} = -\log\left[\sum_{n=1}^{n=i} f(n) \cdot 10^{-w(n) \cdot A(\lambda)th/w}\right], \qquad [2]$$

wherein $A_{(\lambda)th}$ is the calculated theoretical absorbance according to step (2) and $A_{(\lambda)exp}$ is the experimental absorbance according to step (3);

(6) applying the method described in steps 1 to 5 to predict the realistic sun protection factor of a sunscreen preparation prior to it's experimental in vitro or in vivo determination, comprising the following steps:

(7) calculating theoretical UV absorbances $A_{(\lambda)th}$, from 290 to 400nm, in wavelength steps in the range of 1–10 nm, of an UV filter substance or mixture of substances which are contained in wt % amounts $a_1$ to $a_n$ in the sunscreen preparation of step (6), according to equation [1] of step (2);

(8) calculating realistic UV absorbances $A_{(\lambda)real}$, from 290 to 400 nm, in wavelength steps in the range of 1–10 nm, according to the theoretical UV absorbances calculated in step (7) and the mathematical function [2] of step (5), in which the area fractions $f_{(1)}$ to $f_{(i)}$ and the surface densities $w_{(1)}$ to $w_{(i)}$ were previously determined in step (5) for a basic formulation of the same type as the sunscreen preparation under study, by equation $$A_{(\lambda)real} = -\log\left[\sum_{n=1}^{n=i} f(n) \cdot 10^{-w(n) \cdot A(\lambda)th/w}\right] \qquad [2a]$$

(9) calculating realistic sun protection factors (SPF) or broad spectrum indices on basis of the realistic UV absorbance $A_{(\lambda)real}$ determined in step (8).

2. The method according to claim 1, wherein the calculating of realistic sun protection factors of the sunscreen preparation of step (9) follows according to the equation:

$$\text{SPF} = \frac{\sum_{290}^{400} E_\lambda \cdot I_\lambda \cdot \Delta\lambda}{\sum_{290}^{400} E_\lambda \cdot I_\lambda \cdot T_\lambda \cdot \Delta\lambda} \qquad [3]$$

wherein $T\lambda$ is the sunscreen transmittance at wavelength $\lambda$, whereby applies $T_\lambda = 10^{-A(\lambda)real}$, $E_\lambda$ is the spectral irradiance of terrestrial sunlight at wavelength $\lambda$ expected for a clear sky at noon in midsummer for a latitude of 40° N, $I_\lambda$ is the erythema action spectrum.

3. The method according to claim 1, wherein the wave length steps are 5 nm.

4. The method according to claim 1, wherein the error assessment in step (5) is a least squares error assessment.

5. The method according to claim 1, wherein i in equation [2] has a value of 3, with 3 calculated area fractions, $f_{(1)}$, $f_{(2)}$ and $f_{(3)}$ and 3 calculated surface densities $w_{(1)}$ $w_{(2)}$ and $w_{(3)}$.

6. The method according to claim 1, wherein the transparent substrate is excised human epidermis or a synthetic skin substitute.

7. The method of claim 6, wherein said synthetic skin substitute is selected from the group consisting of surgical tape, hydrated collagen film, roughened quartz plate and roughened polymethylmethacrylate plate (PMMA).

8. The method according to claim 1, wherein the calculating of realistic UVA protection factors (PF UVA) of the sunscreen preparation of step (9) is made according to the equation $$\text{PF UVA} = \frac{\sum_{320}^{400} E_\lambda \cdot I_\lambda \cdot \Delta\lambda}{\sum_{320}^{400} E_\lambda \cdot I_\lambda \cdot T_\lambda \cdot \Delta\lambda} \qquad [4]$$

with the same definitions as previously in step (9), except for $I_\lambda$, which is a biological UVA action spectrum.

9. The method according to claim 1, further including calculating a realistic UVA/UVB ratio of the sunscreen preparation according to the equation:

$$\text{UVA/UVB} = \frac{\sum_{320}^{400} A_\lambda real \cdot \Delta\lambda}{\sum_{290}^{320} A_\lambda real \cdot \Delta\lambda} \qquad [5]$$

with the same definitions as previously mentioned.

10. The method according to claim 1, wherein the UV filter substances are selected from a group of organic UV filter substances consisting of octyl methoxycinnamate, octocrylene, octyl salicylate, phenylbenzylimidazole sulfonic acid, 4-methylbenzylidene camphor; dioctyl butamido triazone; isoamyl p-methoxycinnamate, benzophenone-3, benzophenone-4, butyl-methoxydibenzoylmethane, methylene bis-benzoyltriazoyl tetramethylbutyiphenol, homosalate, para amino benzoic acid (PABA), octyl dimethyl PABA, and menthyl anthranilate and mixtures thereof.

11. The method according to claim 1, wherein in step (5) the different area fractions ($f_1$) to ($f_i$) are replaced by an infinite number of area fractions, the sum being F, which is a number between 0 and 1, whereby applies:

$$\int_0^1 dF = 1 \quad \text{and} \quad \int_0^1 W_{(F)} \times dF = w,$$

wherein w is the initial surface density of the sunscreen preparation deposited on the transparent substrate, $W_{(F)}$ being the surface density function, and wherein the mathematical function becomes:

$$A_{(\lambda)exp} = -\log\left[\int_0^1 10^{-W_{(F)} \times A\lambda th/w} \times dF\right] \qquad [2b]$$

and wherein $A_{\lambda,th}$ and $A_{(\lambda)exp}$ have the same meaning as above.

* * * * *